US00PP26906P2

(12) United States Plant Patent
Heemskerk

(10) Patent No.: US PP26,906 P2
(45) Date of Patent: Jul. 5, 2016

(54) ***HEMEROCALLIS* PLANT NAMED 'VER00204'**

(50) Latin Name: ***Hemerocallis* hybrid**
Varietal Denomination: VER00204

(71) Applicant: Gerardus J. C. M. Heemskerk, Noordwijk (NL)

(72) Inventor: Gerardus J. C. M. Heemskerk, Noordwijk (NL)

( * ) Notice: Subject to any disclaimer, the term of this patent is extended or adjusted under 35 U.S.C. 154(b) by 0 days.

(21) Appl. No.: 14/544,489

(22) Filed: Jan. 12, 2015

(51) Int. Cl.
*A01H 5/02* (2006.01)

(52) U.S. Cl.
USPC ..... Plt./312

(58) Field of Classification Search
USPC ..... Plt./263.1, 312
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Hemerocallis* named 'VER00204' that is characterized by its bicolored flowers with petals that are violet rose with a lighter midrib, sepals that are pale yellow to ivory, and a yellow-green throat, its everblooming habit; blooming from June to October in The Netherlands, its compact and dormant plant habit, and its vigorous growth habit.

2 Drawing Sheets

Botanical classification: *Hemerocallis* hybrid.
Cultivar designation: 'VER00204'.

BACKGROUND OF THE INVENTION

The present invention relates to a new and distinct cultivar of *Hemerocallis* plant of hybrid origin, botanically known as *Hemerocallis* 'VER00204' and will be referred to hereafter by its cultivar name, 'VER00204'.

The new cultivar was developed through an on-going breeding program conducted by the Inventor in Noordwijk, The Netherlands. The objectives of the breeding program are to develop new cultivars of *Hemerocallis* that are everblooming with compact plant habits in a range of flower colors.

The new cultivar arose from crosses made in summer of 2006. Proprietary seed parent lines were pollinated with a mixture of pollen collected from proprietary pollen parents and the collected seeds were pooled and sown for evaluation. 'VER00204' was selected as a single unique plant from the resulting seedlings in summer of 2009. The specific parents are unknown and none of the possible parent plants are named or patented.

Asexual propagation of the new cultivar was first accomplished by division in Noordwijk, The Netherlands in 2009 by the Inventor. Asexual propagation by division and tissue culture has determined that the characteristics of this cultivar are stable and are reproduced true to type in successive generations.

SUMMARY OF THE INVENTION

The following traits have been repeatedly observed and represent the characteristics of 'VER00204'. These attributes in combination distinguish 'VER00204' as a new and distinct cultivar of *Hemerocallis*.

1. 'VER00204' exhibits bicolored flowers with petals that are violet rose with a light midrib, sepals that are pale yellow to ivory, and a yellow-green throat.

2. 'VER00204' exhibits an everblooming habit; blooming from June to October in The Netherlands.
3. 'VER00204' exhibits a compact and dormant plant habit.
4. 'VER00204' exhibits a vigorous growth habit.

The new cultivar can be most closely compared to the *Hemerocallis* hybrid cultivars 'Frans Hals' (not patented) and 'Longfields Butterfly' (not patented). 'Frans Hals' is similar to 'VER00204' in having bicolored flowers. 'Frans Hals' differs from 'VER00204' in having a taller flower scape, a shorter flowering period, and in flowers that are orange toned, and in having a semi-evergreen plant habit. 'Longfields Butterfly' is similar to 'VER00204' in having a dormant plant habit. 'Longfields Butterfly' differs from 'VER00204' in having flowers that are pinker in color with a yellow throat.

BRIEF DESCRIPTION OF THE DRAWINGS

The accompanying colored photographs illustrate the overall appearance and distinct characteristics of the new *Hemerocallis*. The photographs were taken of a 6 month-old plant of the new cultivar as field grown in Noordwijk, The Netherlands and placed in a container for the photographs.

The photograph in FIG. 1 provides a side view of 'VER00204' in bloom.

Figure 1:
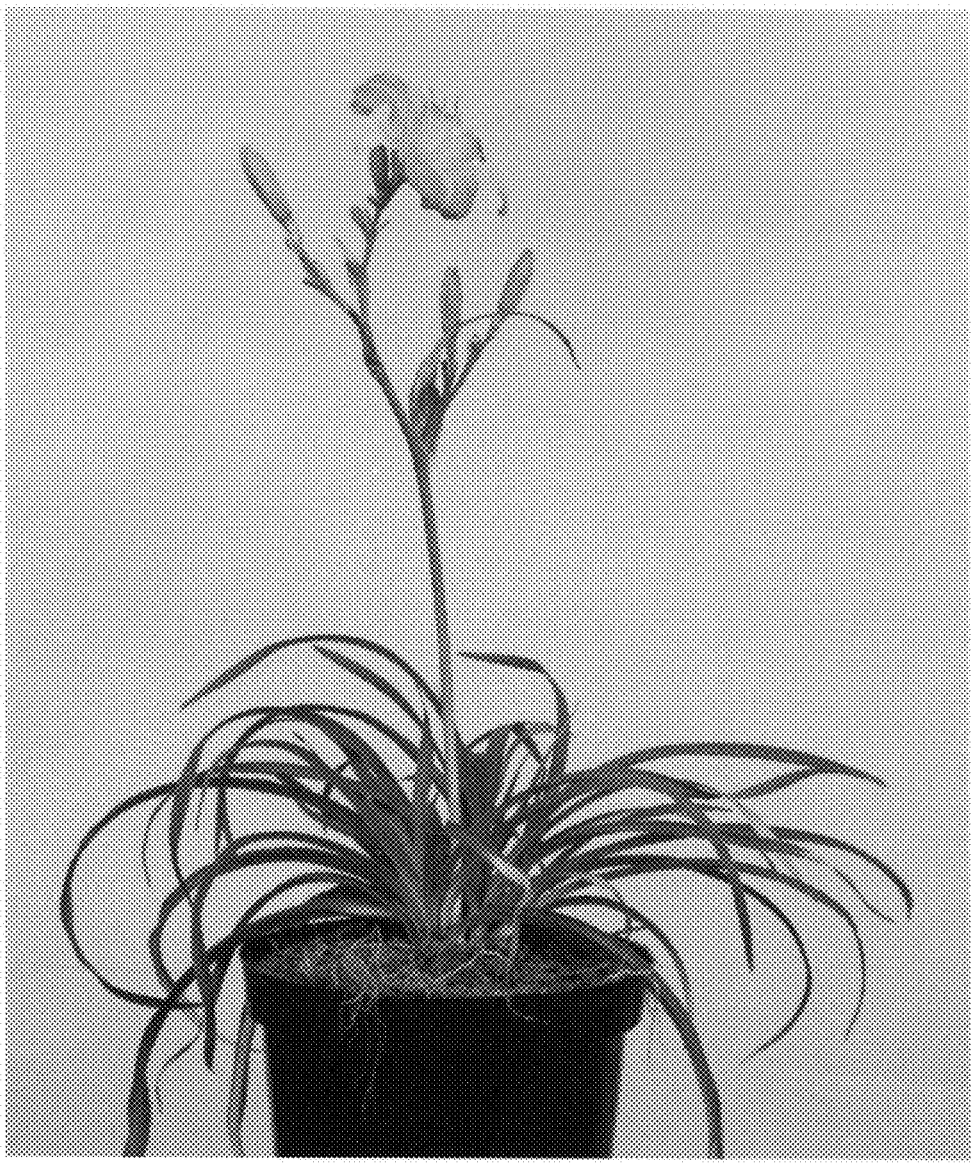
Figure 2:
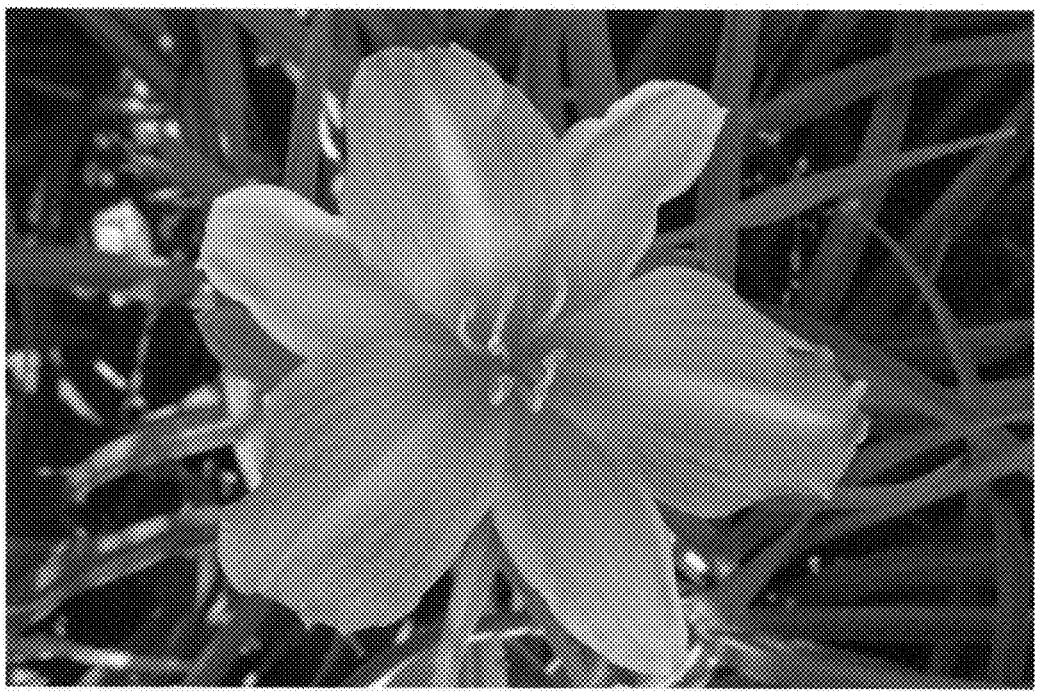

The photograph in FIG. 2 provides a close-up view of a flower of 'VER00204'.

Figure 3:
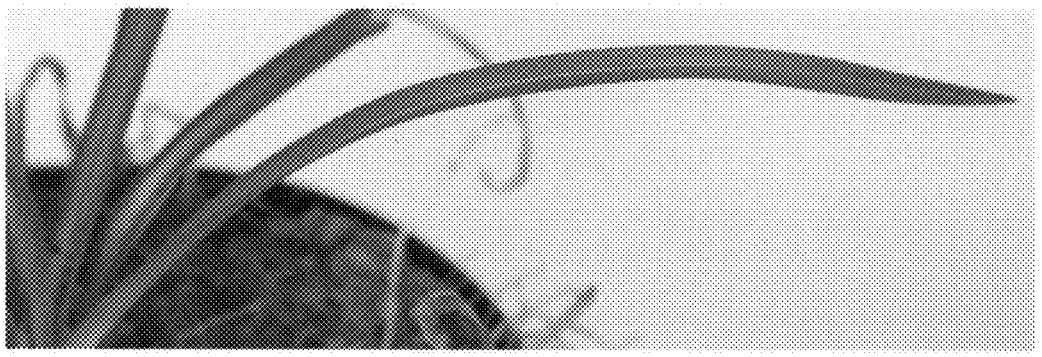

The photograph in FIG. 3 provides a close-up view of a leaf of 'VER00204'.

The colors in the photographs are as close as possible with the digital photography and printing techniques utilized and the color codes in the detailed botanical description accurately describe the new *Hemerocallis*.

DETAILED BOTANICAL DESCRIPTION OF THE PLANT

The following is a detailed description of 6 month-old plants of the new cultivar as field grown in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—Everblooming from June to October in The Netherlands.

*Plant type.*—Herbaceous perennial, dormant type.

*Plant habit.*—Compact, basal rosette, grass-like foliage.

*Height and spread.*—An average of 38 cm in height to top of foliage and 55 cm in height to top of inflorescence and 40 cm in spread (after two years in the garden).

*Hardiness.*—At least in U.S.D.A. Zone 5.

*Diseases.*—No disease resistance or susceptibility has been observed.

*Root description.*—Fibrous roots.

*Propagation.*—Division and tissue culture.

*Growth rate.*—Vigorous; a single fan division will finish in a 11-cm container in an average of 4 months and as a field grown bare-root division in an average of 8 months.

*Stem description.*—Basal rosette, no lateral branches present.

Foliage description:

*Leaf shape.*—Linear, strongly carinate.

*Leaf division.*—Simple.

*Leaf base.*—Decurrent.

*Leaf apex.*—Long acute with a short apiculate tip.

*Leaf venation.*—Parallel, color upper and lower surface; 143A.

*Leaf margins.*—Entire, slightly undulate.

*Leaf attachment.*—Decurrent, no petioles.

*Leaf arrangement.*—Basal rosette, equitant, fan-shaped.

*Leaf orientation.*—Pendulant.

*Leaf surface.*—Both surfaces glabrous, upper surface moderately glossy, lower surface matte.

*Leaf color.*—Young leaves upper and lower surface; 143A, mature leaves upper surface; a color between 137B and 146A, mature leaves lower surface; a color between 143A and 146A.

*Leaf size.*—An average of 30.4 cm in length and 1.1 cm in width.

*Leaf quantity.*—Average of 8 per rosette.

Flower scape description (peduncle):

*Scape shape.*—Slightly triangular.

*Scape number.*—1 per fan at one time, continuously produced during bloom season.

*Scape aspect.*—Straight, held at an average angle of 85° to soil level.

*Scape size.*—An average of 32.9 cm in length and 5 mm in diameter.

*Scape color.*—144A.

*Scape surface.*—Glabrous, slight sheen.

*Scape branching.*—None.

Flower description:

*Inflorescence type.*—Scape bearing a terminal panicle of single flowers.

*Inflorescence size.*—An average of 11.9 cm in width and 17 cm in depth.

*Lastingness of flowers.*—About 24 hours, self cleaning.

*Flower size.*—An average of 8.5 cm in depth and 9.0 cm in diameter.

*Flower fragrance.*—None detected.

*Flower shape.*—Campanulate, single.

*Flower number.*—An average of 12 flowers and buds per scape.

*Flower aspect.*—Upright to outward.

*Flower bud.*—Oblanceolate in shape, an average of 4 cm in length and 1 cm in width, color; N144B with top N144A.

*Rate of flower opening.*—About 10% of flowers open at a time, about 4 weeks for all flowers to open per scape.

*Flower attachment.*—Pedicellate.

*Petals.*—3, obovate to elliptic in shape, an average of 7.8 cm in length and 3.8 cm in width, margins entire and moderately crinkled, apex retuse, base fused (lower 22%), both surfaces glabrous, dull, and slightly velvety, color; upper surface when opening and when fully open; a blend of 70C and 85A on wide margins and apex, center stripe 13A (main vein), and tube (throat) 154C, lower surface when opening and when fully open; 13B suffused with 167D and tube N144A, color not fading.

*Sepals.*—3, rotate in arrangement, average of 7.3 cm in length, 2.2 cm in width, oblanceolate in shape, entire margins, base cuneate with lower portion fused (23%), acute apex, color; upper surface when opening and when fully open; 14A tinged N144D at the base with tube 154C, lower surface when opening and when fully open; 14A to 14B tinged N144D at the center with apex 143B and tube N144A, both surfaces glabrous, matte, and slightly velvety.

*Calyx.*—Rotate in arrangement, an average of 3.9 cm in length and 8.3 cm in diameter.

*Pedicels.*—An average of 5 mm in length and 0.2 mm in diameter, strong strength, color; 143A, held at an angle of 35° to peduncle, glabrous surface.

*Pedicel leaf.*—Average of 1 per pedicel, broadly lanceolate in shape, a blend of 144A and 157C in color on both surfaces, average of 1.7 cm in length and 1.3 cm in width, sheathed base, narrowly acuminate apex, glabrous on both surfaces.

Reproductive organs:

*Gynoecium.*—Pistil; 1, style; 8.0 cm in length, 14B with 150B to 150C at the base in color, stigmas; crested, 153D in color, and 1 mm in length, ovary; oblong in shape, 144A in color.

*Androecium.*—Stamens; 6, anthers; narrowly oblong in shape, dorsifixed, 6 mm in length and 177A in color; filament; 3.9 cm in length, 14B in color, pollen; moderate to high in quantity and 17A in color.

*Fruit/seeds.*—None observed.

It is claimed:

1. A new and distinct cultivar of *Hemerocallis* plant named 'VER00204' as herein illustrated and described.

* * * * *